(12) United States Patent
Dansaert et al.

(10) Patent No.: US 7,445,116 B2
(45) Date of Patent: Nov. 4, 2008

(54) SHARPS DISPOSAL CONTAINER

(75) Inventors: John Dansaert, Solana Beach, CA (US); Ken Stark, San Marcos, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 463 days.

(21) Appl. No.: 10/539,002

(22) PCT Filed: Dec. 16, 2003

(86) PCT No.: PCT/US03/39900

§ 371 (c)(1), (2), (4) Date: Jun. 15, 2005

(87) PCT Pub. No.: WO2004/060178

PCT Pub. Date: Jul. 22, 2004

(65) Prior Publication Data

US 2006/0070898 A1   Apr. 6, 2006

Related U.S. Application Data

(60) Provisional application No. 60/433,842, filed on Dec. 16, 2002.

(51) Int. Cl.
*B65D 83/10* (2006.01)

(52) U.S. Cl. .................. 206/366; 206/459.1; 220/254.3; 220/324

(58) Field of Classification Search ......... 206/363–366, 206/370, 1.5, 459.1; 220/201, 254.3, 254.7, 220/324, 326, 837, 908
See application file for complete search history.

(56) References Cited

U.S. PATENT DOCUMENTS

| | | | | |
|---|---|---|---|---|
| 5,322,164 A * | 6/1994 | Richardson et al. | ......... | 206/366 |
| 5,409,113 A * | 4/1995 | Richardson et al. | ......... | 206/366 |
| 5,573,113 A * | 11/1996 | Shillington et al. | ......... | 206/366 |
| 6,253,916 B1 * | 7/2001 | Bickel | ......... | 206/366 |
| 6,691,867 B1 * | 2/2004 | Bickel et al. | ......... | 206/366 |
| 6,761,283 B1 * | 7/2004 | Gilliam et al. | ......... | 220/254.3 |

* cited by examiner

*Primary Examiner*—Luan K Bui
(74) *Attorney, Agent, or Firm*—Jeanne P. Lukasavage

(57) ABSTRACT

A sharps disposable container (10) comprises a base (12) having a bottom wall (23) and a sidewall extending upwardly therefrom defining a receptacle. A top having an aperture (42) therethrough is connected to an upper portion (16) of the sidewall. A closure (48) is hingedly connected to the top and capable of moving from an open position which allows access to the aperture and a closed position wherein the closure releasably engages the top. A gripping tab (54) is hingedly connected to the closure and projects upwardly from the closure when the closure is in the closed position and releasably engages the top. The closure can be permanently locked to the top by pivoting the gripping tab in a downwardly position and moving the closure to the closed position.

24 Claims, 16 Drawing Sheets

SHARPS DISPOSAL CONTAINER

This application claims priority from U.S. Provisional Application No. 60/433,842 filed on Dec. 16, 2002.

BACKGROUND OF THE INVENTION

The present invention relates to sharps disposal containers.

The safe and efficient disposal of sharps such as surgical knives, blades, hypodermic needles and the like is a problem for medical and other healthcare facilities. Disposable containers have been developed in recent years which provide a reasonably high degree of security for disposable sharps articles and materials from hospitals and clinics. Many of these articles, such as needles and surgical blades known as sharps, and other similar articles and materials, must be disposed of in a manner to keep them out of the hands of unauthorized persons and to keep them from being reused.

The containers are normally designed to prevent the removal of materials from the container under ordinary circumstances until permanently closed. The permanent closure is normally present on the container and often used as a temporary cover until the container is filled and ready for permanent closure. However, the permanent closure is frequently unintentionally placed in the permanent position prior to completely filling the container. This results in unnecessary waste of containers and unnecessary cost. Therefore, it is desirable that the container be completely filled prior to permanent closure for disposal.

There is a need for a closure that may be safely used as a temporary closure without the problem of unintentionally placing it in the permanent closure position. There is a further need for a container have a solid sturdy base that provides a leak-proof seal between the lid and base.

SUMMARY OF THE INVENTION

The present invention provides an improved closure with a gripping tab that may be safely used as a temporary closure without the danger of unintentionally placing it in the permanent closure position. The gripping tab aligns itself to an upwardly directed position during temporary closure, to act as indicia that the closure is not full and the gripping tab is projecting downwardly when the closure is in the locked position. The present invention further provides secondary locking structure to more vigorously secure the closure to the top to protect against exposure of the collected sharps during rough handling of the filled locked sharps disposal container.

A sharps disposal container comprises a base having a bottom wall and a sidewall extending upwardly from the bottom wall defining a receptacle for receiving sharps. A top having an aperture therethrough is connected to an upper portion of the sidewall of the base. A closure is hingedly connected to the top and capable of moving to and from an open position which allows access to the aperture for placing sharps in the receptacle and a closed position covering the aperture wherein the closure releasably engages the top. A gripping tab is hingedly connected to the closure and projects substantially upwardly from the closure when the closure is in a closed position to indicate that the closure is not permanently locked to the lid and to provide grippable structure for overcoming the releasable engagement forces to gain access to the receptacle. Additional structure is provided for locking the closure to the top when the gripping tab is moved to a downwardly directed position and the closure is moved to its closed position.

Locking structure may include a discontinuity on the gripping tab configured to engage a discontinuity on the top. The discontinuity on the gripping tab may be a projection and a discontinuity on the top may also be a projection or an aperture positioned so that when the closure is moved to the closed position, the portion of the gripping tab containing the projection is forced through the aperture.

Secondary locking structure is preferably provided. At least one secondary locking structure to lock the closure to the top when it is in the closed position and said griping tab is in its downwardly directed position is provided. The secondary locking structure may include a discontinuity on the closure configured for locking engagement with the discontinuity on the top. A preferred secondary locking structure includes a flexible projection on the closure and a ledge on the lid positioned for engagement with the flexible projection. At least two secondary locking structures are preferred. These structures may be positioned on opposite sides of the closure.

The aperture in the top may include a plurality of downwardly facing flexible fingers for helping to prevent reflux of sharps in the receptacle. The lid may also include at least one elongate port for needle removal which is covered by the closure when the closure is in the closed position.

To promote a liquid-tight sealing engagement between the base and the top the upper portion of the side wall of the base includes an outwardly curved rim and the top includes a rim around its periphery wherein the rim of the base and the rim of the top are configured to engage each other in an interference fit to prevent separation of the top and the base, the top is held to the base in a snap-fit arrangement by a plurality of inwardly directed projections on the rim of the top engaging the rim of the base. Other structures may be used to hold the top and the base together along with adhesives, ultrasonic welding and the like.

The base also includes a carry handle flexibly connected to the base and having a rest position along a front wall of the base and pivotable to a position over the top of the sharps collector when lifted upwardly.

It is preferred that the closure is hingedly connected to the top through a living hinge and the gripping tab is hingedly connected to the closure through a living hinge. It is also preferred that the top and the closure including the gripping tab and the secondary locking structure are integrally molded of thermoplastic material and that the base and the carry handle are also integrally molded of thermoplastic material.

The present invention further provides a base that is both sturdy and provide an efficient, leak proof seal with the lid.

DETAILED DESCRIPTION

Figure 1:
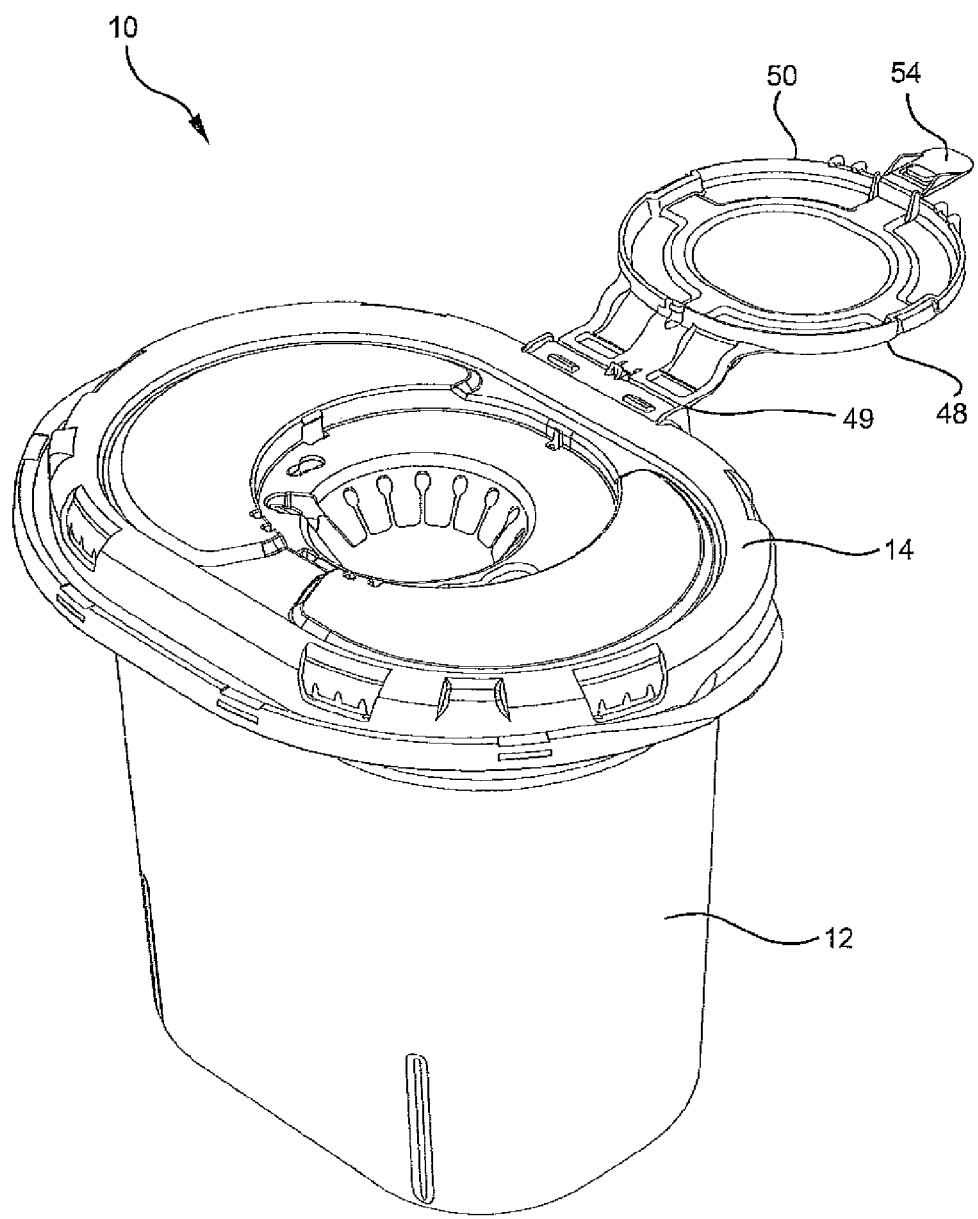
FIG. 1 is a perspective view of a sharps disposal container of the present invention shown with the closure in an open position.
Figure 2:
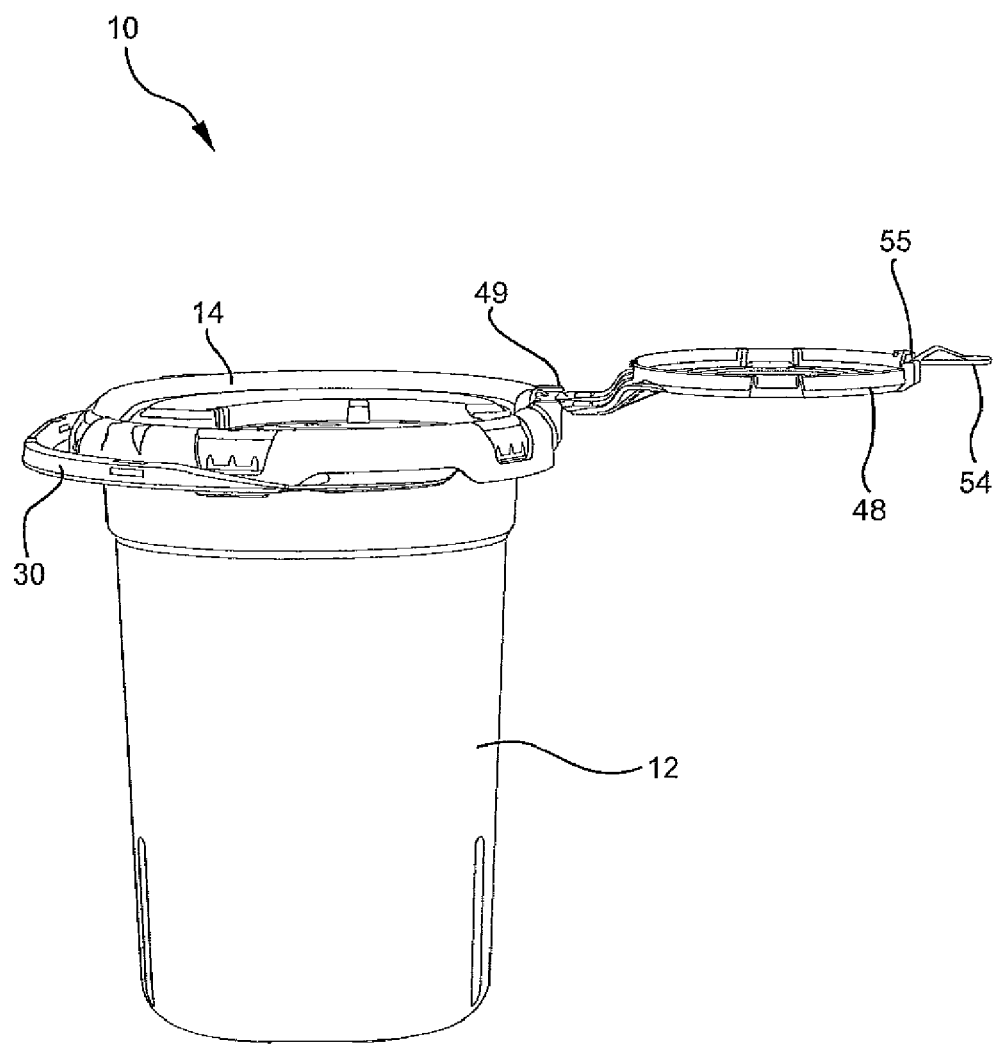
FIG. 2 is a side elevation view of the sharps disposal container of FIG. 1.
Figure 3:
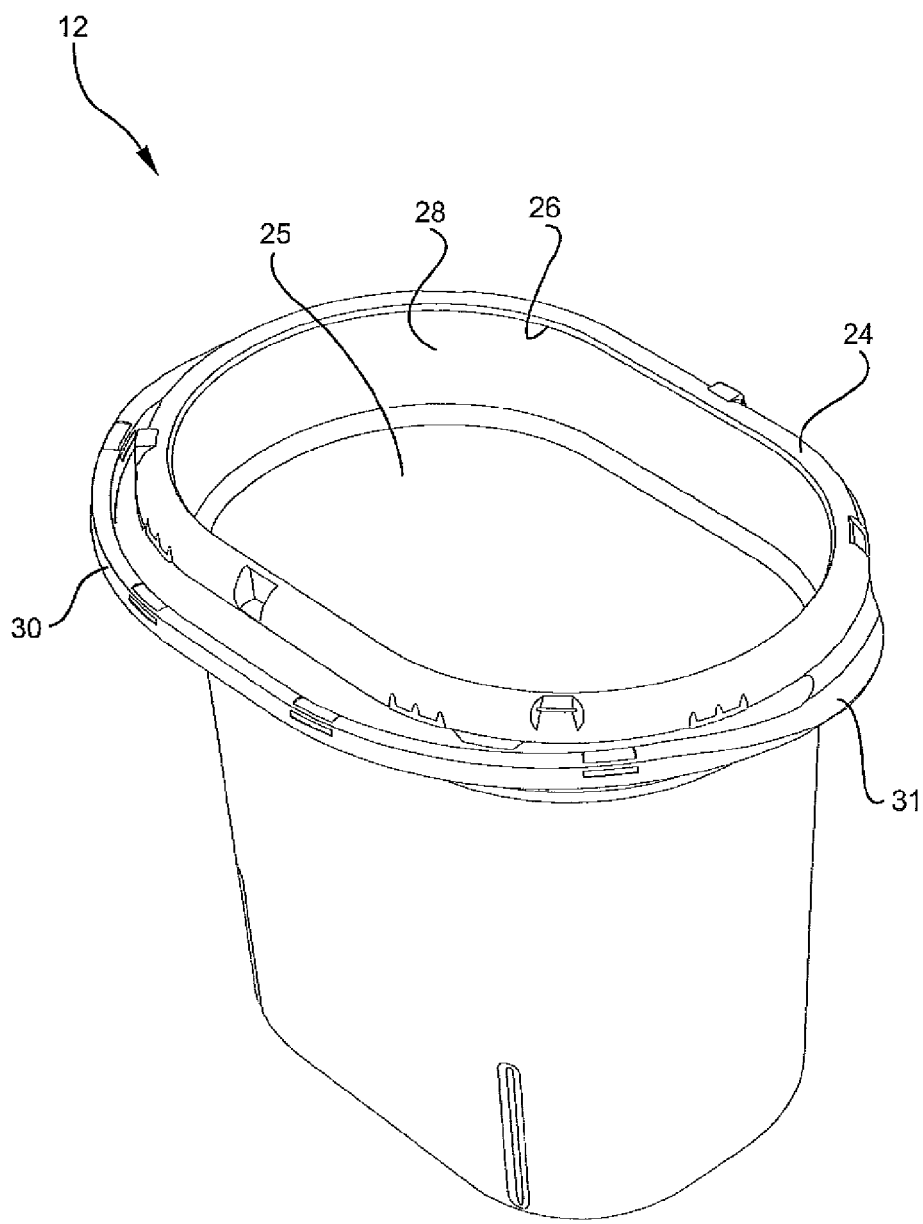
FIG. 3 is a perspective view of a base of the sharps disposal container of FIG. 1.
Figure 4:
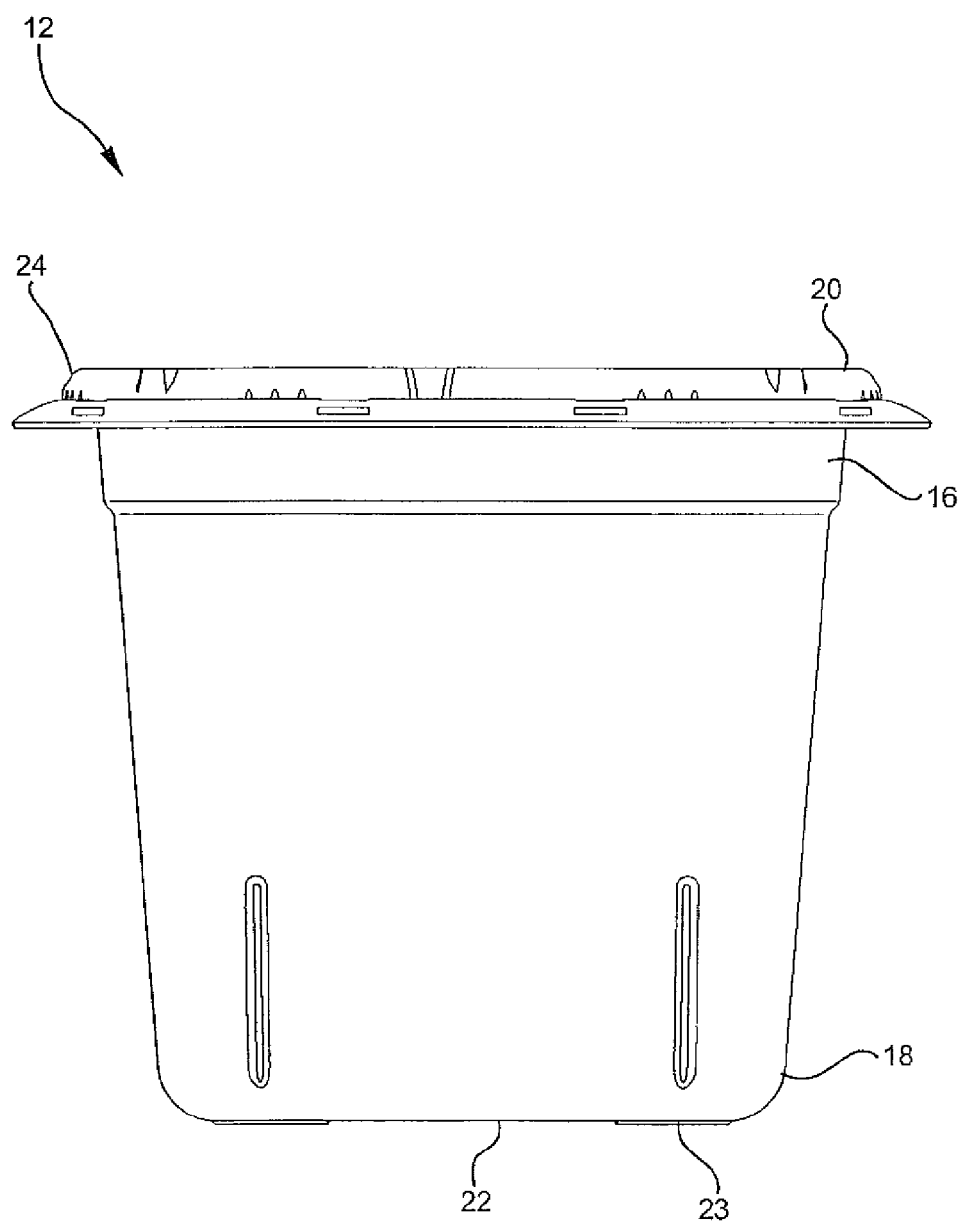
FIG. 4 is a front elevation view of the base of FIG. 3.
Figure 5:
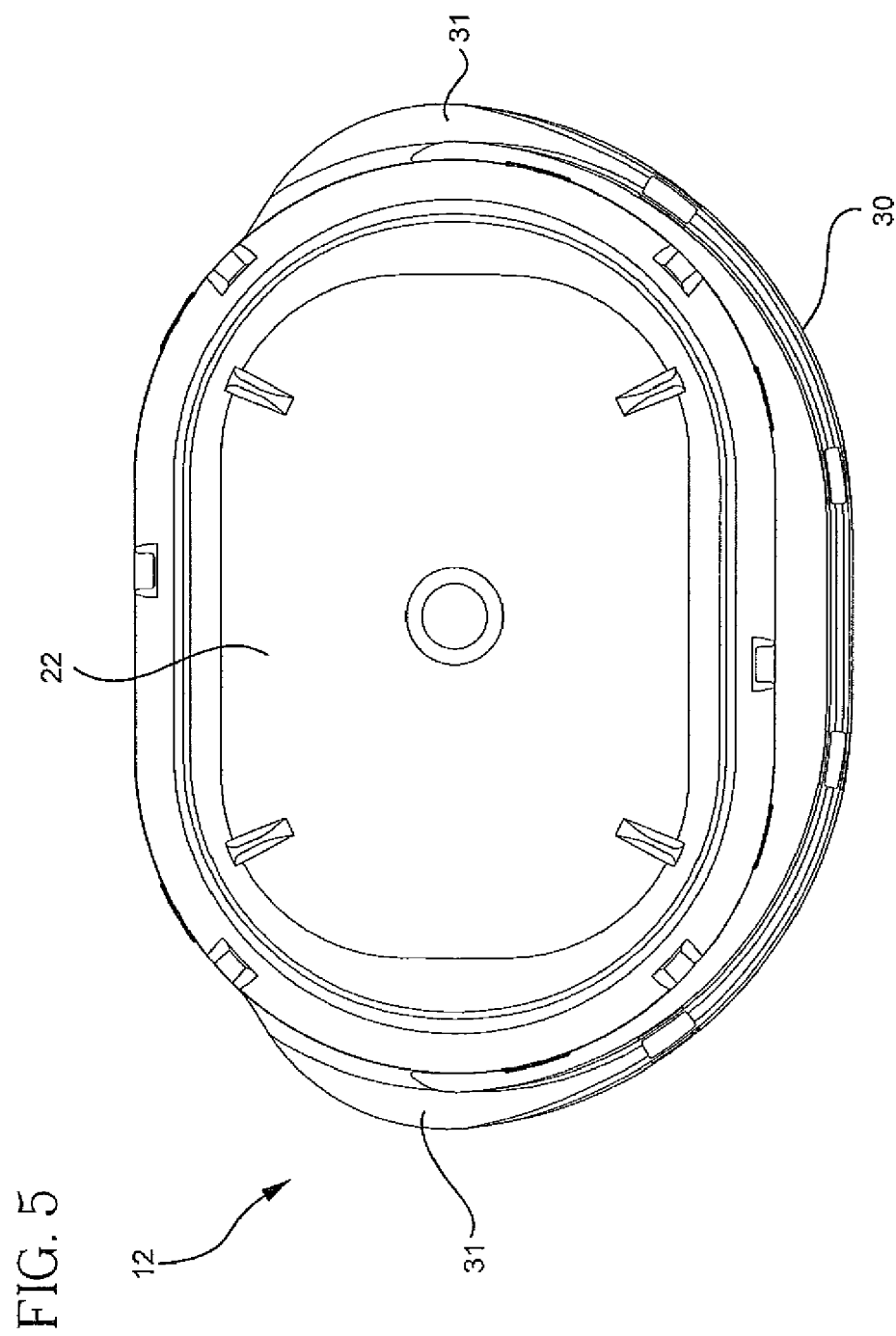
FIG. 5 is a top plan view of the base of FIG. 3.
Figure 6:
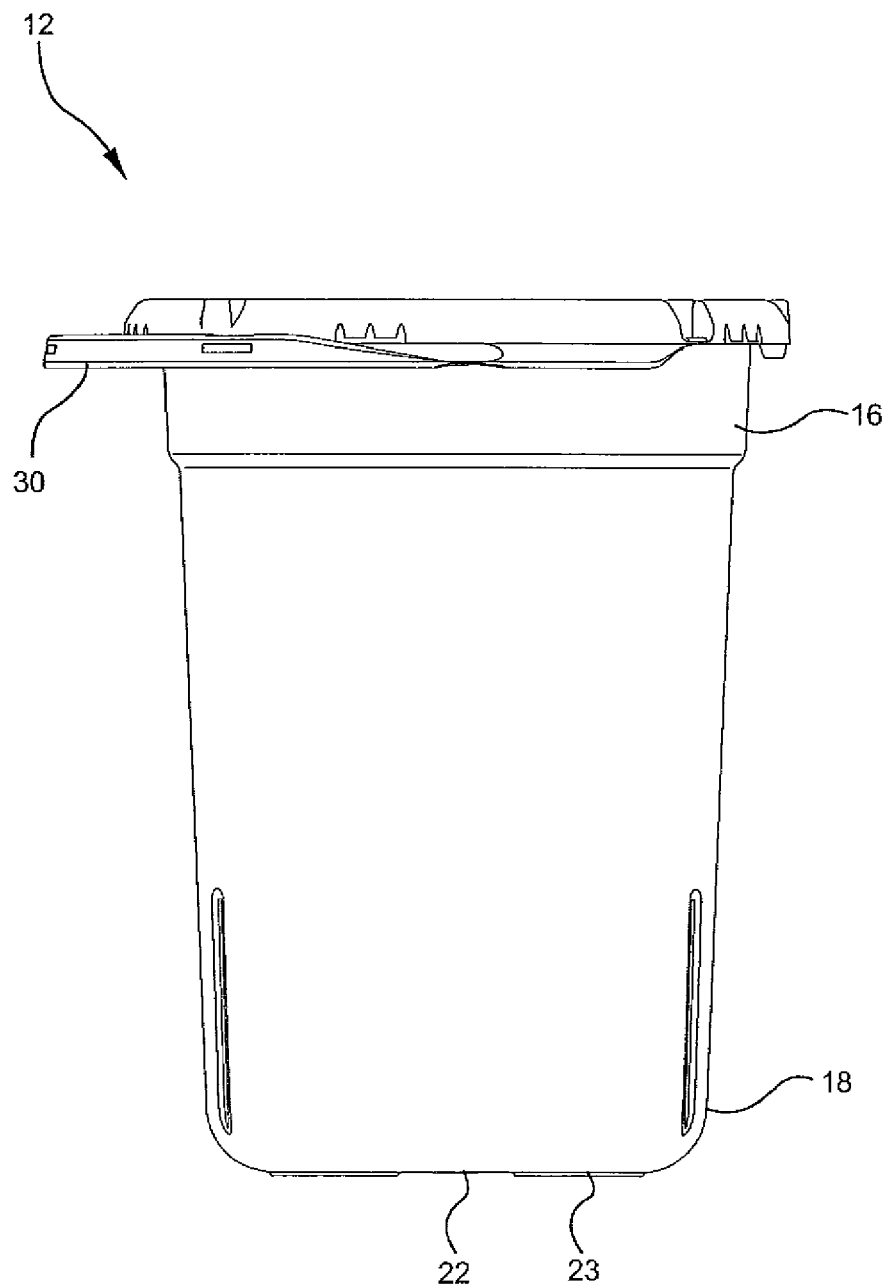
FIG. 6 is a side elevation view of the base of FIG. 3.
Figure 7:
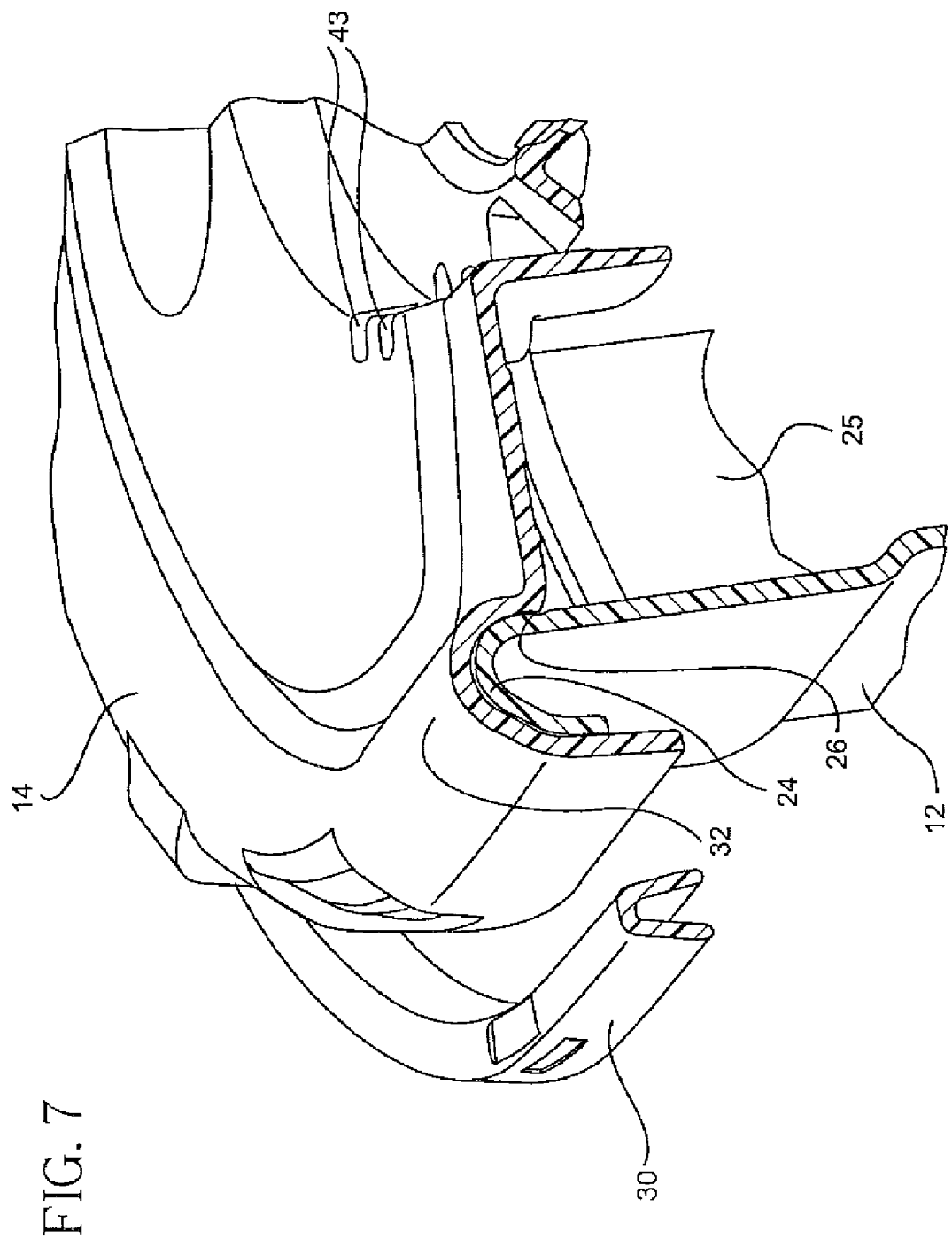
FIG. 7 is a cross-sectional perspective view of the sealing feature of the top and base of the sharps disposal container of FIG. 1.
Figure 8:
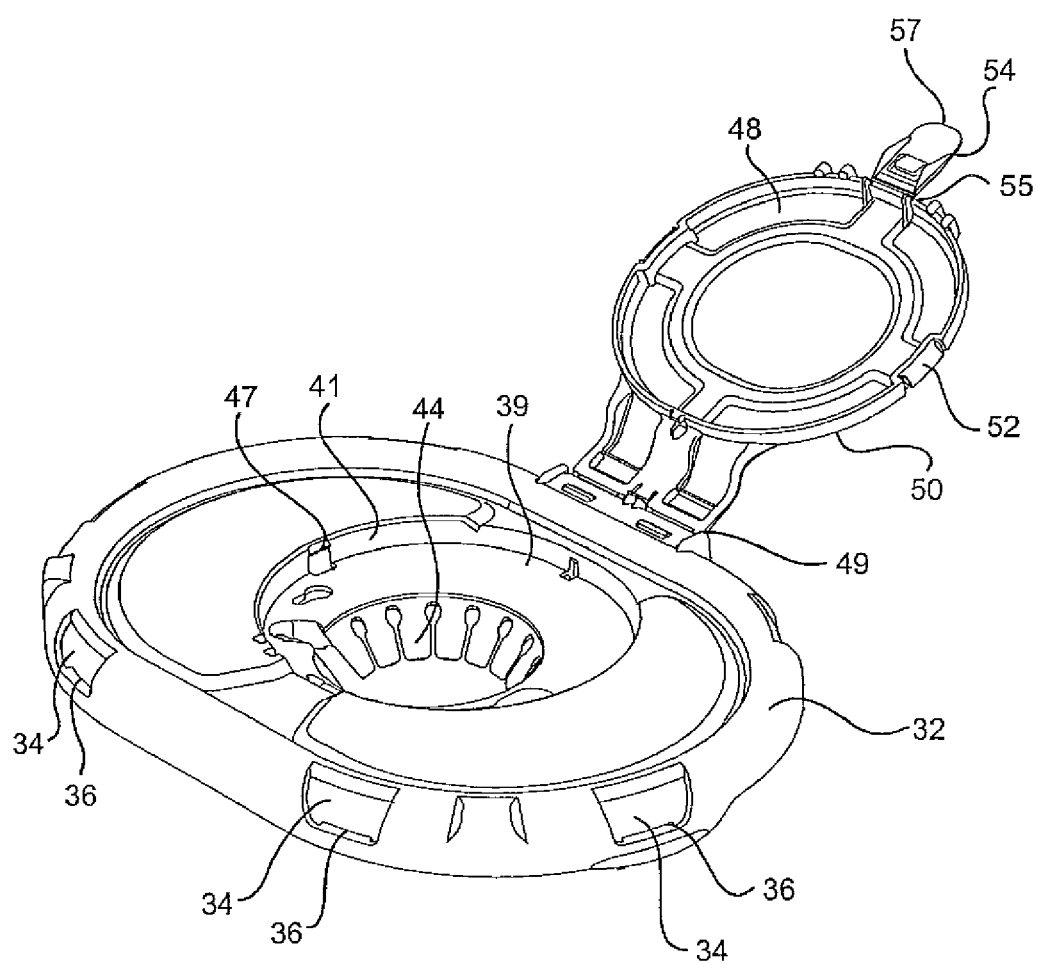
FIG. 8 is a perspective view of the lid of the sharps disposal container of FIG. 1.
Figure 9:
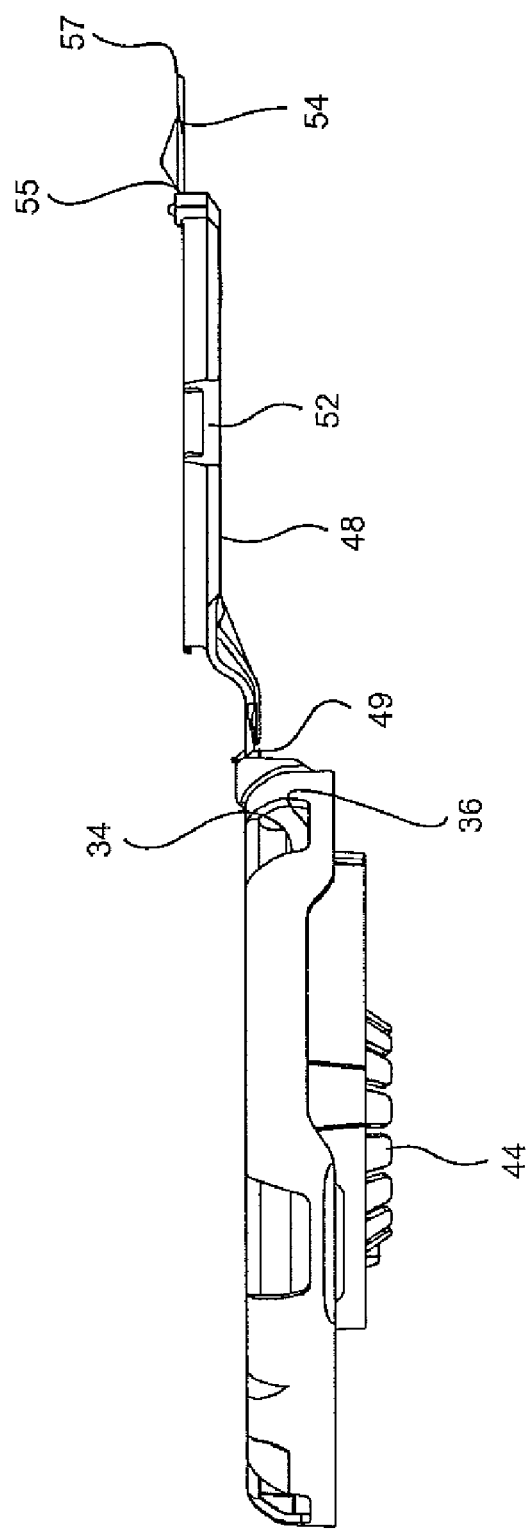
FIG. 9 is a side elevation view of the lid of FIG. 8.
Figure 10:
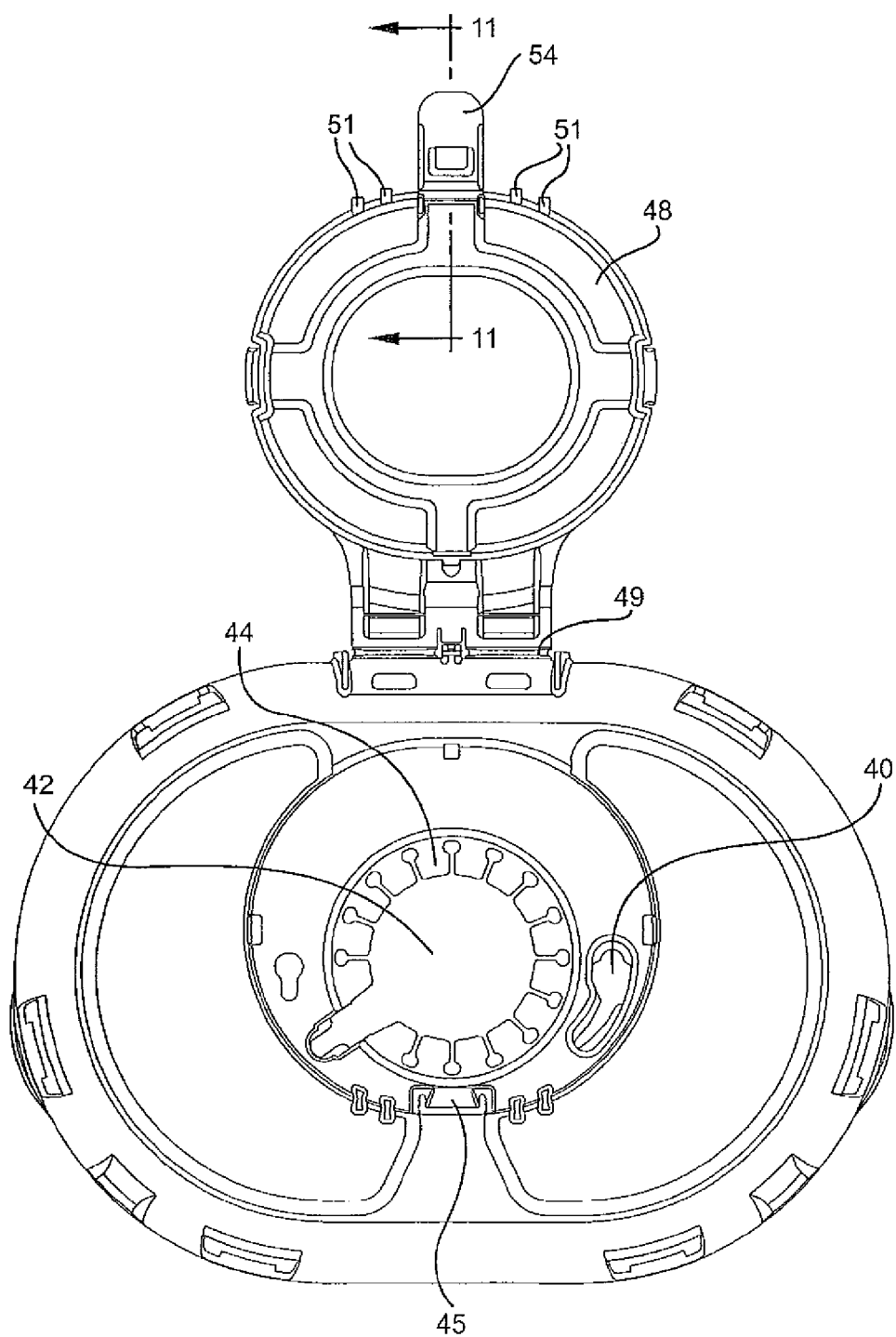
FIG. 10 is a top plan view of the lid of FIG. 8.
Figure 11:
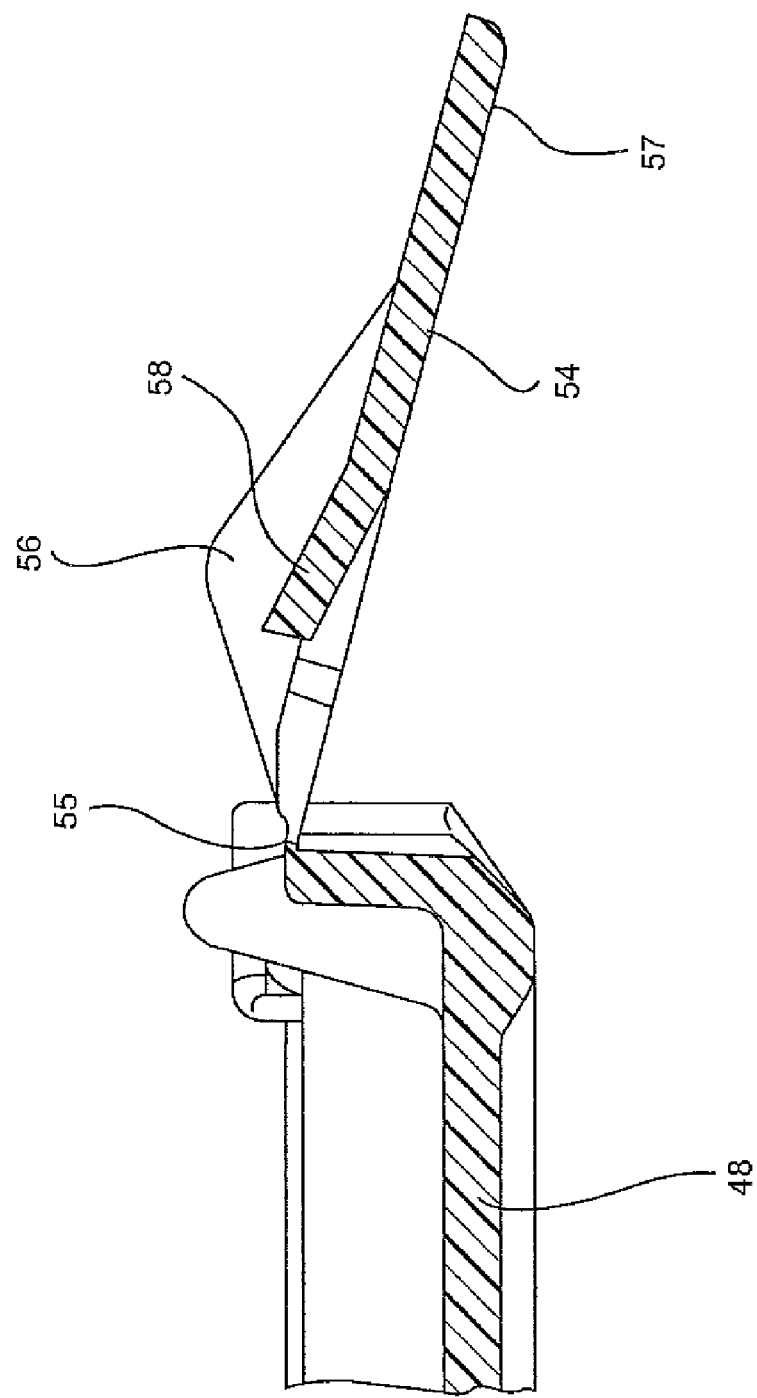
FIG. 11 is an enlarged cross-sectional side-elevation view of the closure and gripping tab taken along line 11-11 in FIG. 10.
Figure 12:
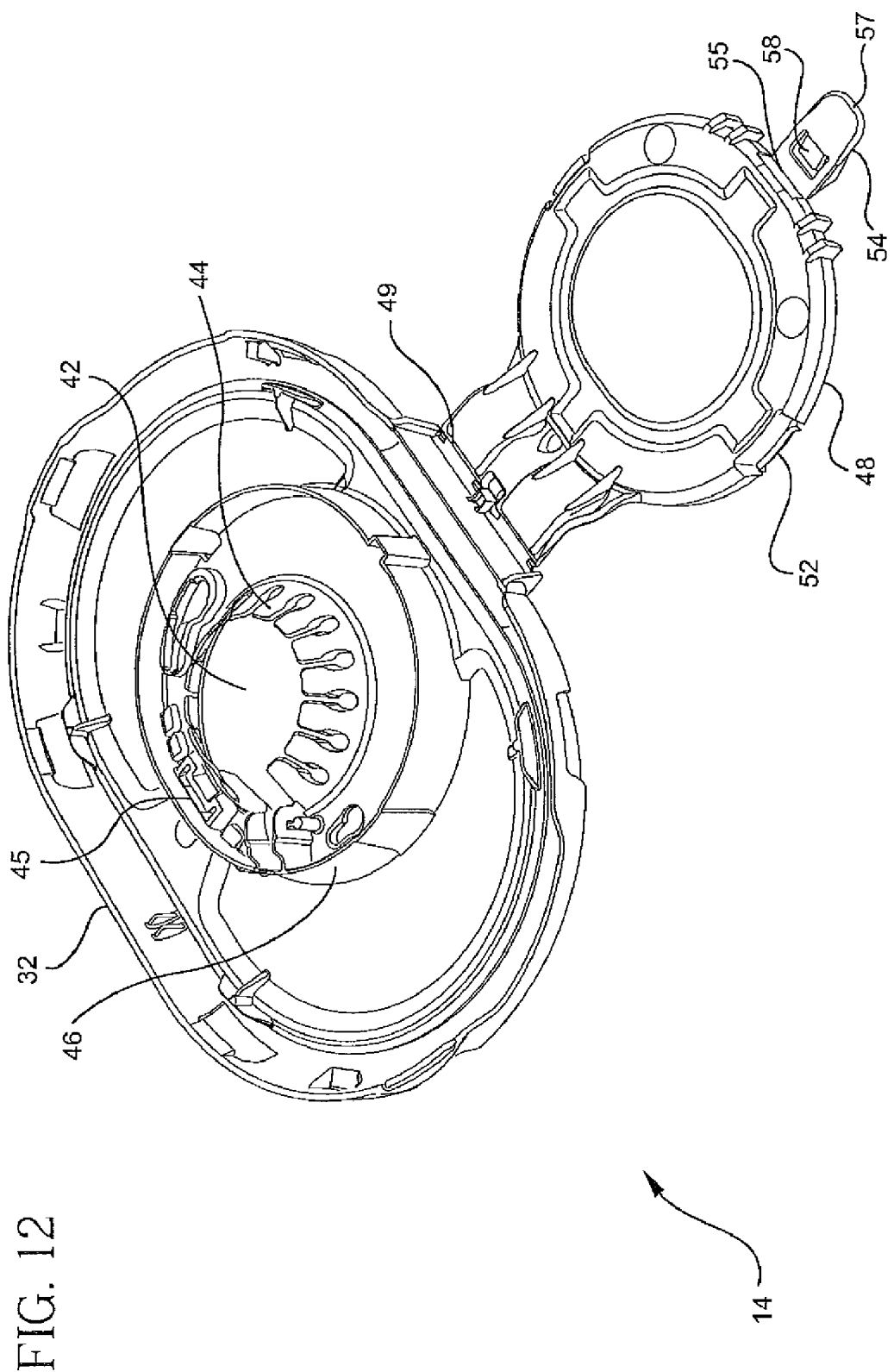
FIG. 12 is a bottom perspective view of the lid of FIG. 8.
Figure 13:
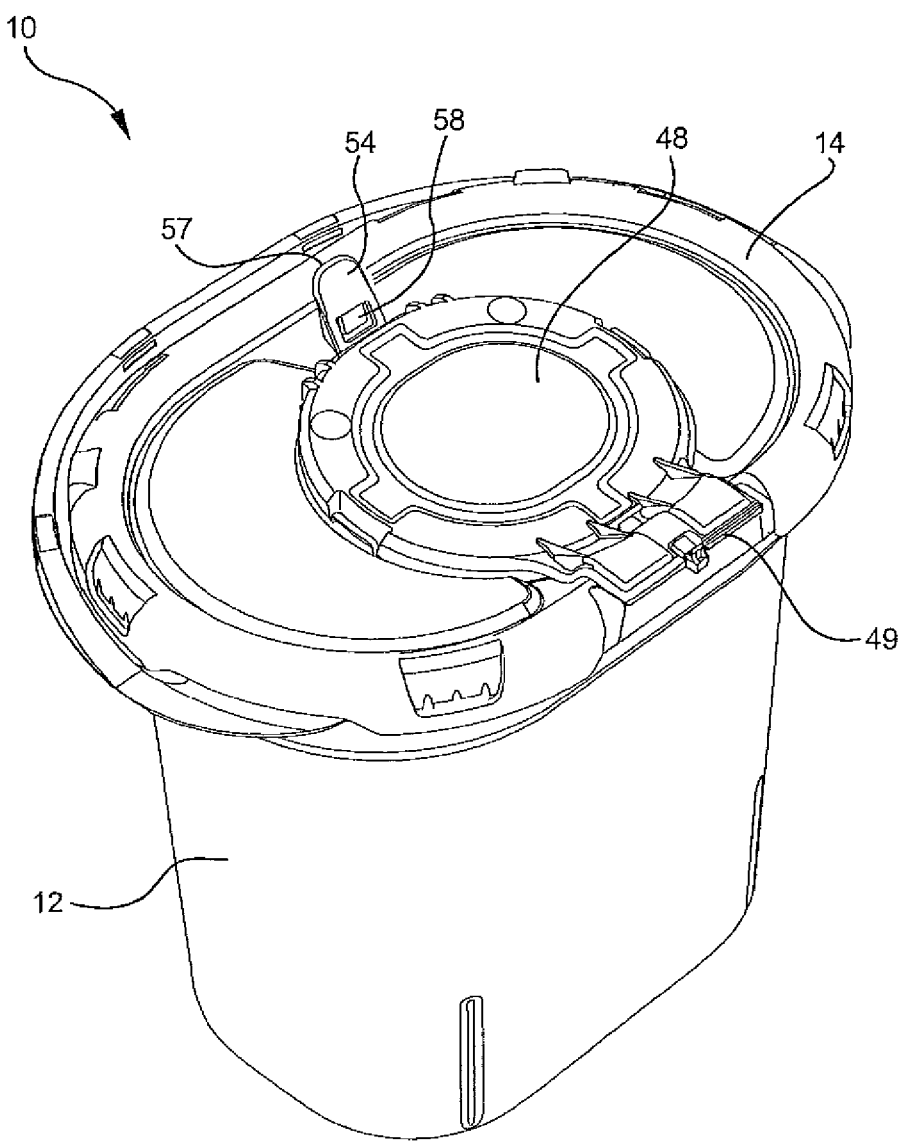
FIG. 13 is a perspective view of the sharps disposal container with the closure in the temporarily closed position.
Figure 14:
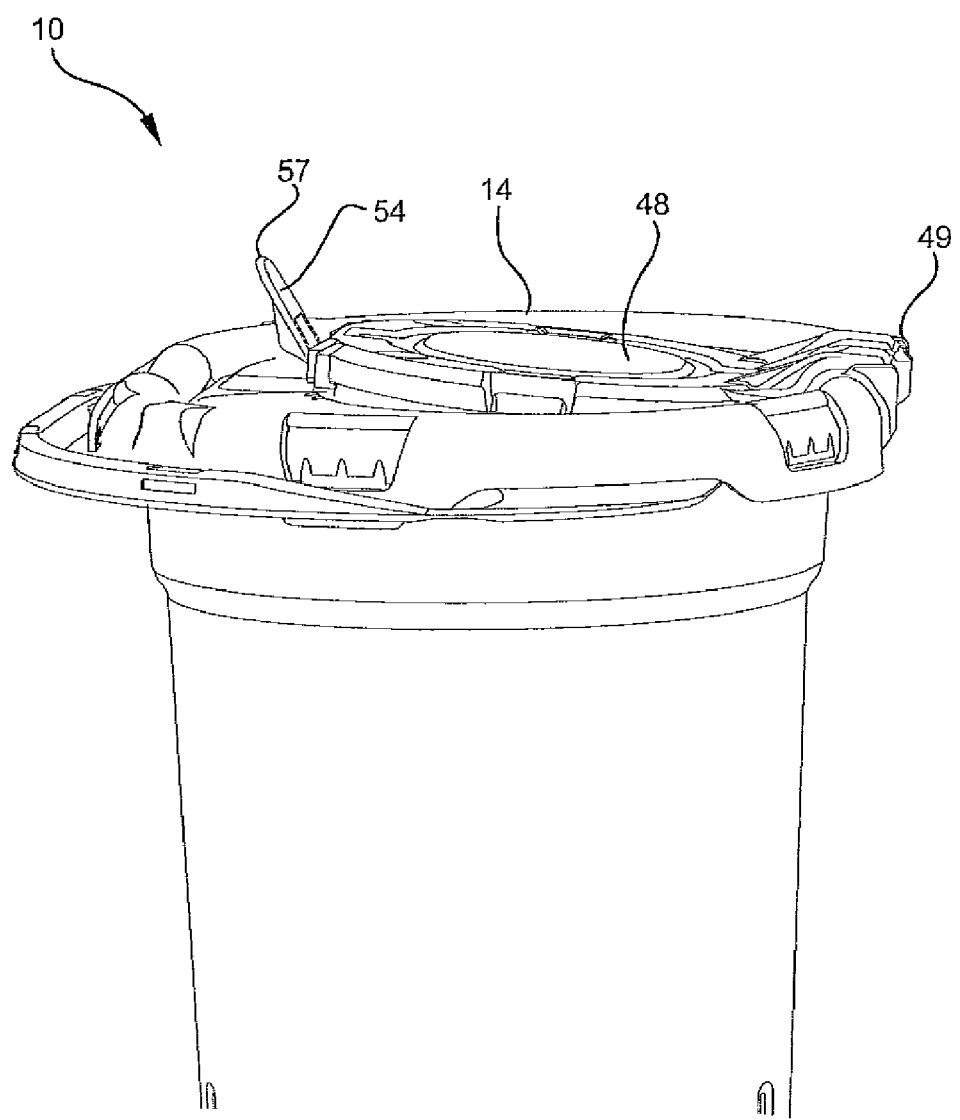
FIG. 14 is a side elevation view of the sharps disposal container of FIG. 13.
Figure 15:
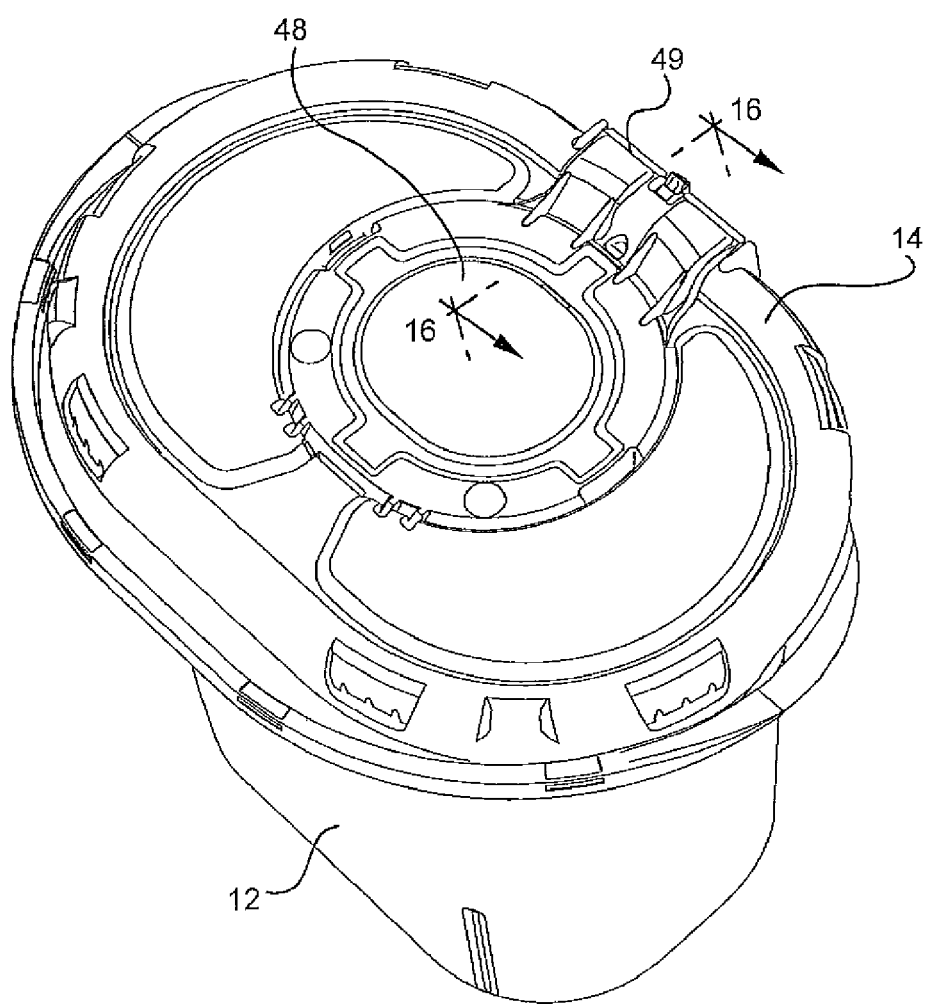
FIG. 15 is a perspective view of the sharps disposal container of FIG. 13 with the closure in the permanently closed position.
Figure 16:
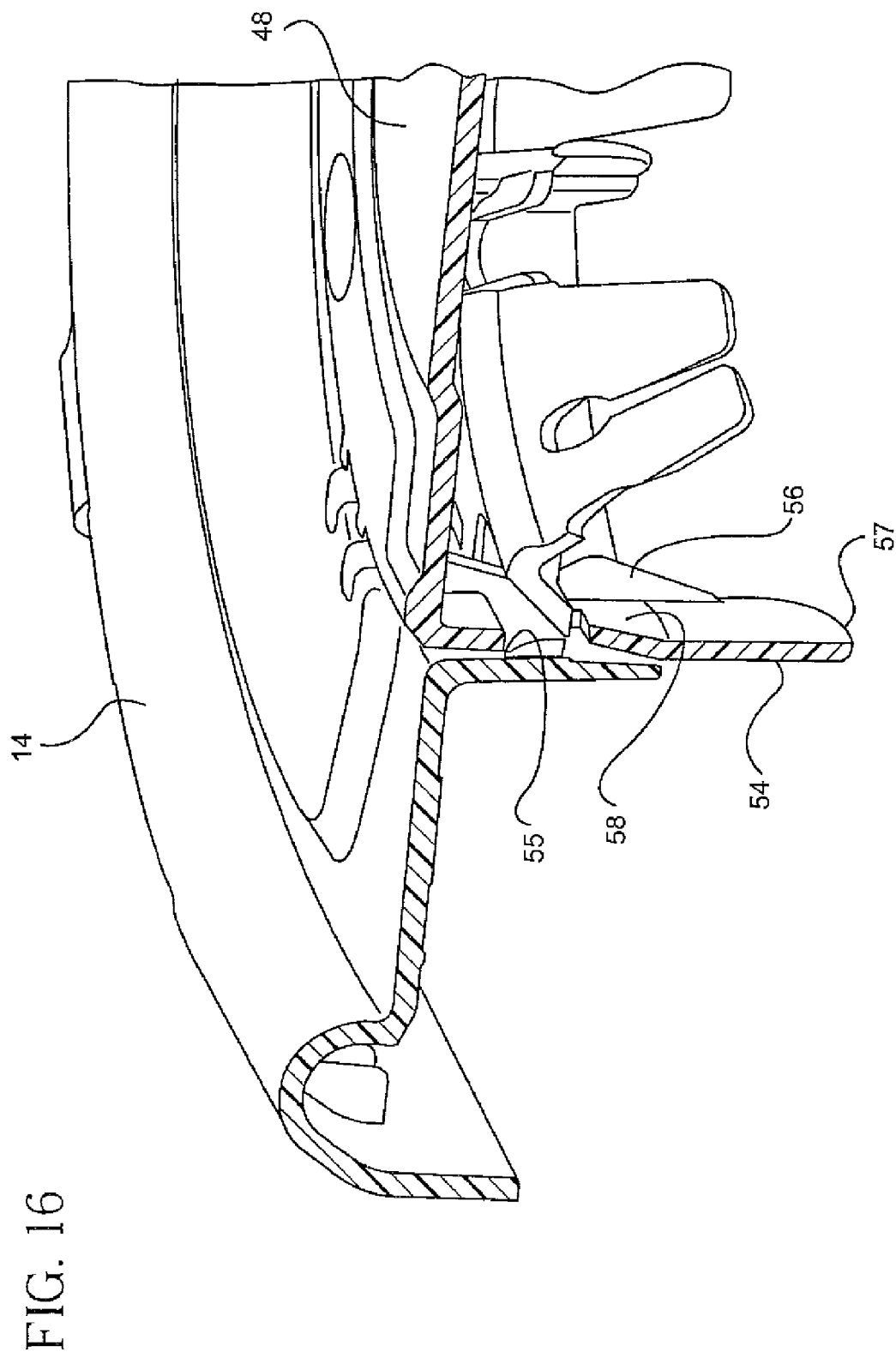
FIG. 16 is an enlarged cross-sectional view of the lid taken along line 16-16 of FIG. 15.

Referring to FIGS. 1-16, a sharps disposal container 10 comprises a base 12 and a top or lid 14. The base includes an upper portion 16 being generally oval or elliptical in shape and a lower portion 18 being generally rectangular in shape, but having rounded edges. The present invention contemplates the shape of the base gradually changing in shape from the upper portion to the lower portion from a more circular shape, such as an oval, ellipse or circle to a shape defining more straight lines, such as a rectangle or square. The rounded lines of the upper portion provides a leak resistant seal with the base while the straight lines of the lower portion square provides for a sturdy container resistant to forces that would cause the container to fall on its side.

As best illustrated in FIGS. 3-6, base 12 defines upper portion 16 having an open end 20 and lower portion 18 having a closed end 22 including bottom wall 23, defining a receptacle 25 for receiving sharps. An outwardly curved rim 24 surrounds the periphery of the open end 20. A projection 26 extends from an interior wall 28 of base 12 at the top of the upper portion 16. The projection 26 may be continuous around the interior wall of the base or it may comprise a series of projections distributed around the interior wall the base. The base further includes a carry handle 30 that is pivotable between a generally horizontal position as shown to a generally vertical position. In this preferred embodiment handle 30 is integrally molded with base 12 and includes flexible portions 31 which allow the handle to pivot from a horizontal position to a generally vertical position. It is preferred that the base and handle be made of thermoplastic material such as polypropylene. The handle may be made pivotable by having a generally flexible structure throughout or in select areas, such as flexible portions 31, or by having a hinge or like structure. All of these structures are within the purview of the present invention and the flexible portions illustrated are merely representative of these many possibilities.

As best illustrated in FIGS. 8-12, top 14 of sharps disposal container 10 includes rim 32 defining a plurality of openings 34. Each of the openings 34 include an extension 36 extending from the bottom of the opening toward rim 24 of base 12. Rim 32 of lid 14 engages rim 24 of base 12 to form container 10. Lid 14 will snap onto the base via extensions 36 engaging the edge of rim 24 of the base. Additionally, projection 26 on rim 24 forms an interference fit with the base to provide a leak proof seal between the lid and the base.

The top further includes access structure that provides access to the receptacle. Access structure preferably includes at least one elongate needle port 40 to which needles may be removed from medical devices and deposited in the receptacle and an aperture 42 through which all other debris, such as syringes, may be deposited in the receptacle. A plurality of flexible fingers 44 extend downwardly and inwardly around the periphery of aperture 42. The flexible fingers help prevent reflux of debris out of the access structure once the debris is in the container. An aperture 45 having ledge 47 is provided at one edge of the main opening. The access structure further includes a dam 46 extending downwardly around needle port 40 and aperture 42. In the event that the sharps disposal container is accidentally overturned, the dam helps keep liquid in the receptacle from exiting through the aperture.

A cap or closure 48 is hingedly attached to top 14 by closure hinge 49. The closure is capable of moving to and from an open position which allows access to the aperture for placing sharps in the receptacle and a closed position covering the aperture wherein the closure engages the top to releasably hold the closure in the closed position. Releasable engagement between the closure and the top can be achieved by a variety of structures such as making all or part of outside diameter 50 of the closure larger than inside wall 41 of recess 39 in the top. In this embodiment, projections 51 on closure 48 frictionally engage slots 43 in inside wall 41 of the top. The projections may be wider than the slots or positioned for slight misalignment to obtain the desired releasable frictional engagement. The releasable engagement of the closure to the top may also be accomplished with any combination of projections and recesses to produce a frictional and/or a weak snap-fit engagement of the closure and the top.

A gripping tab 54 having a free end 57 is connected to the closure via tab hinge 55. The gripping tab includes a cam surface 56 and a projection in the form of locking barb 58 thereon.

An important feature of the present invention is that the closure may be positioned in temporary removable engagement with the top covering the aperture or permanently locked to the top. It is desirable to temporarily cover the aperture when sharps are not being placed in the receptacle. When it is determined that the receptacle is full and the container is no longer usable, the closure may be permanently locked to the top, sealing the aperture. Further, the tab is designed to position itself for easy grasping to overcome the releasable engagement of the closure to the top. Also, before the closure is permanently locked to the top the gripping tab projects upwardly to show the user that the closure is not permanently locked.

In use, sharps and other debris are placed in the receptacle through aperture 42 and/or needle slot 40. Between uses, the closure is moved into its closed position covering the aperture wherein it releasably engages the lid. Closing of the closure causes cam surface 56 to contact portions of recess 39 causing the tab to rotate upwardly into a substantially vertical position where it is easy to grip and overcome the releasable engagement to gain access to the aperture for subsequent disposal of sharps. When the receptacle is full, the user pivots the gripping tab to a downward orientation with respect to the closure and pivots the closure into the closed position so that the gripping tab enters side aperture 45 and locking barb 58 snaps past ledge 47 in side aperture 45 to permanently lock the closure in the closed position. At this point, the free end of the gripping tab is no longer visible indicating to the user that the sharps disposal container is full and locked and ready for disposal.

Another important advantage of the present invention is the presence of multiple locking structures to secure the closure to the top. This is important since after the container is full and the closure is locked to the top, unusually rough treatment of the container may cause the closure to pivot or move with respect to the top partially exposing the interior of the receptacle to the environment. It is desirable to have at least one secondary locking structure and preferably to have two to lock the closure to the top when the closure is in the closed position and the gripping tab is In the downwardly directed position. In this embodiment there are two secondary locking structures comprising flexible projections 62 on the sides of the closure, preferably on opposite sides. Flexible projections engage ledges 47 in the inside wall of recess 39 to lock the closure to the top. It is intended that the interaction between flexible protections 52 and ledge 47 will be ineffective or releasable before the closure is placed in the closed locked position with the tab facing downwardly.

It is preferred that openings 34 containing extensions 36 are positioned in an asymmetrical fashion so that the top can only be connected to the base so that the gripping tab of the closure is closer to carry handle which rests along a front wall of the base than to a back wall of the base.

The invention claimed is:

1. A sharps disposal container comprising:
    a base having a bottom wall and a sidewall extending upwardly from said bottom wall defining a receptacle for receiving sharps;
    a top having an aperture therethrough connected to an upper portion of said side wall;
    a closure hingedly connected to said top and capable of moving to and from an open position which allows access to said aperture for placing sharps in said receptacle and a closed position covering said aperture wherein said closure releasably engages said top; and
    a gripping tab hingedly connected to said closure and projecting upwardly from said closure when said closure is in said closed position, for moving said closure to said open position, and means for locking said closure to said top when said gripping tab is moved to a downwardly directed position and said closure is moved to said closed position.

2. The sharps disposal container of claim 1 wherein said means for locking includes a discontinuity on said gripping tab configured to engage a discontinuity on said top.

3. The sharps disposal container of claim 2 wherein said discontinuity on said gripping tab is a projection and said discontinuity on said top is a projection.

4. The sharps disposal container of claim 2 wherein said discontinuity on said gripping tab is a projection and said discontinuity on said lid is an aperture positioned so that when said closure is moved to said closed position a portion of said gripping tab containing said projection is forced through said aperture.

5. The sharps disposal container of claim 1 having at least one secondary locking structure to lock said closure to said top when said closure is in said closed position and said gripping tab is in said downwardly directed position.

6. The sharps disposal container of claim 5 wherein said at least one secondary locking structure includes a discontinuity on said closure configured for locking engagement with a discontinuity on said top.

7. The sharps disposal container of claim 5 wherein said secondary locking structure is a flexible projection on said closure and a ledge on said lid positioned for engaging said flexible projection.

8. The sharps disposal container of claim 5 wherein said at least one secondary locking structure comprises two secondary locking structures.

9. The sharps disposal container of claim 8 wherein said two secondary locking structures are positioned on opposite sides of said closure.

10. The sharps disposal container of claim 1 wherein said aperture includes a plurality of downwardly facing flexible fingers for helping to keep sharps in said receptacle.

11. The sharps disposal container of claim 1 wherein said top includes at least one elongate port for needle removal, said at least one port being covered by said closure when said closure is in said closed position.

12. The sharps disposal container of claim 1 wherein said upper portion of said side wall includes an outwardly curved rim and said top includes a rim around its periphery wherein said rim of said base and said rim of said top are configured to engage each other in an interference fit for sealing engagement between said top and said base.

13. The sharps disposal container of claim 12 wherein said top is held to said base in a snap-fit arrangement achieved by a plurality of Inwardly directed projections on said rim of said top engaging said rim of said base.

14. The sharps disposal container of claim 12 wherein said base includes a carry handle flexibly connected to said base and having a rest position along a front wall of said base and pivotable to a position over said top when lifted upwardly.

15. The sharps disposal container of claim 14 wherein said handle and said base are integrally molded of thermoplastic material.

16. The sharps disposable container of claim 14 wherein said rim of said top and said rim of said base are configured so that said top can only engage said base in an orientation where said gripping tab is closer to said front wall of said base.

17. The sharps disposal container of claim 5 wherein said top and said closure including said gripping tab and said secondary locking structure are integrally molded of thermoplastic material.

18. The sharps disposal container of claim 5 wherein said closure is hingedly connected to said top through a living hinge.

19. The sharps disposal container of claim 5 wherein said gripping tab is hingedly connected to said closure through a living hinge.

20. A sharps disposal container comprising:
    a base having a bottom wall and a sidewall extending upwardly from said bottom wall defining a receptacle for receiving sharps;
    a top having an aperture therethrough connected to an upper portion of said side wall;
    a closure hingedly connected to said top and capable of moving to and from an open position which allows access to said aperture for placing sharps in said receptacle and a closed position covering said aperture wherein said closure releasably engages said lid;
    a gripping tab hingedly connected to said closure and projecting upwardly from said closure when said closure is in said closed position for moving said closure to said open position, and a discontinuity on said gripping tab configured to engage a discontinuity on said top for locking said closure to said top when said gripping tab is moved to a downwardly directed position and said closure is moved to said closed position; and
    at least one secondary locking structure to lock said closure to said top when said closure is in said closed position and said gripping tab is in its downwardly directed position.

21. The sharps disposal container of claim 20 wherein said secondary locking structure is a flexible projection on said closure and a ledge on said lid positioned for engaging said flexible projection.

22. The sharps disposal container of claim 20 wherein said at least one secondary locking structure comprises two secondary locking structures.

23. A sharps disposal container of claim 20 wherein said top and said closure including said gripping tab and said secondary locking structure are integrally molded of thermoplastic material.

24. A sharps disposal container comprising:
- a base having a bottom wall and a sidewall extending upwardly from said bottom wall defining a receptacle for receiving sharps;
- a top having an aperture therethrough connected to an upper portion of said sidewall, said aperture including a plurality of downwardly and inwardly facing fingers for helping to keep sharps in said receptacle;
- said upper portion of said side wall including an outwardly curved rim and said top including a rim around its periphery wherein said rim of said base and said rim of said top are configured to engage each other in an interference fit for sealing engagement between said top and said base;
- a closure hingedly connected to said top and capable of moving to and from an open position which allows access to said aperture for placing sharps in said receptacle and a closed position covering said aperture wherein said closure releasably engages said lid;
- a gripping tab hingedly connected to said closure and projecting upwardly from said closure when said closure is in said closed position, for moving said closure to said open position, and a discontinuity on said gripping tab configured to engage a discontinuity on said top for locking said closure to said top when said gripping tab is moved to a downwardly directed position and said closure is moved to said closed position;
- at least one secondary locking structure to lock said closure to said top when said closure is in said closed position and said gripping tab is in its downwardly directed position; and
- said top and said closure including said gripping tab and said secondary locking structure being integrally molded of thermoplastic material.

* * * * *